US006890912B2

(12) United States Patent
Lyles

(10) Patent No.: US 6,890,912 B2
(45) Date of Patent: May 10, 2005

(54) SUNSCREEN FORMULATIONS CONTAINING NUCLEIC ACIDS

(76) Inventor: Mark B. Lyles, 9127 Cap Mountain Dr., San Antonio, TX (US) 78255

(*) Notice: Subject to any disclaimer, the term of this patent is extended or adjusted under 35 U.S.C. 154(b) by 17 days.

(21) Appl. No.: 09/910,485

(22) Filed: Jul. 20, 2001

(65) Prior Publication Data

US 2002/0064508 A1 May 30, 2002

Related U.S. Application Data

(60) Provisional application No. 60/220,094, filed on Jul. 21, 2000.

(51) Int. Cl.$^7$ .......................... A61K 7/42; A61K 31/70; C07H 21/04
(52) U.S. Cl. ........................... 514/44; 536/23.1; 424/59
(58) Field of Search ....................... 424/59; 536/23.1; 514/44

(56) References Cited

U.S. PATENT DOCUMENTS

| | | | | |
|---|---|---|---|---|
| 4,474,763 A | * | 10/1984 | Lubowe | ........................ 514/21 |
| 4,707,353 A | | 11/1987 | Bugaj et al. | |
| 4,707,354 A | | 11/1987 | Garlen et al. | |
| 5,194,253 A | | 3/1993 | Garrido | |
| 5,547,684 A | | 8/1996 | Vainberg et al. | |
| 5,662,889 A | | 9/1997 | Vainberg et al. | |
| 5,709,877 A | | 1/1998 | Della Valle et al. | ........ 424/444 |
| 5,985,333 A | | 11/1999 | Vainberg et al. | |
| 5,989,535 A | | 11/1999 | Nayak | ..................... 424/78.02 |
| 6,117,846 A | * | 9/2000 | Li | .............................. 514/44 |
| 6,147,056 A | * | 11/2000 | Gilchrest et al. | ............. 514/44 |

FOREIGN PATENT DOCUMENTS

| | | | | |
|---|---|---|---|---|
| DE | 4323615 A | 1/1995 | | |
| FR | 2 511 243 | 2/1983 | | |
| FR | 2 634 374 | 1/1990 | | |
| GB | 2 233 557 B | 1/1991 | ............ | A61K/7/42 |
| WO | 98/00894 | 2/1990 | ............ | A61K/7/42 |
| WO | WO 95/01773 | 1/1995 | | |
| WO | WO 96/01617 | 1/1996 | | |
| WO | WO 98/38966 | 9/1998 | | |
| WO | WO 99/51197 | 10/1999 | | |
| WO | WO 00/54743 | 9/2000 | | |
| WO | WO 01/58418 | 8/2001 | | |

OTHER PUBLICATIONS

Sigma catalog # D7290,Deoxyribonucleic Acid for Hybridization, Sigma Chemical Company.*
Ananthaswamy et al., Inhibition of solar simulator–induced p53 mutations and protection against skin cancer development in mice by sunscreens, Journal of Investigative Dermatology, vol. 112, pp. 763–768.*
Botwell, Research Division Laboratory Manual,1998.*
ChemGenes'to *"Excellence in Ultra Pure RNA and DNA Synthesis"* at internet address <http://www.chemgenes.com/about.html>3 Pages, Jun. 26, 2000.

Dog and Kennel's *"Humane Society of the United States Offers Tips to Protect Pets During Summer Months"* at internet address <http://www.dogandkennel.com/news/hsus01.shtml>2 Pages, Aug. 29, 2001.
Yao–Ping Lu et al.'s *"Tropical applications of cafferine or (–)–epigallocatechin gallate (EGCG) inhibit carcinogenesis and selectively increase apoptosis in UVB–induced skin tumors in mice"* PNAS vol. 99 No. 19 pp 12455–12460, Sep. 17, 2002.
Chemical Abstracts Service, Columbus, Ohio; XP002195478; No. 1.966M; Title.
Drouin & Therrien, "UVB–induced cyclobutane pyrimidine dimer frequency correlates with skin cancer mutational hotspots in p53," Photochemistry & Photobiology, vol. 66, No. 5, Nov. 1997, pp. 719–726.
"The UV Spectrum of nucleotide bases," available at http://www.genevue.com/A_DNA/UVspectrum_2.html., printed May 2, 2000.
"Anthiocyanins protect DNA from UV damage," available at http://www.agron.missouri.edu/mnl/66/169stapleton.html (1992).
The U.S., Global Change Research Information Office, "Introduction," available at http://www.gcrio.org/UNEP1998/UNEP98p13.html, printed May 2, 2000.
The U.S., Global Change Research Information Office, "Effects on the skin," available at http://www.gcrio.org/UNEP1998/UNEP98p15.html, printed May 2, 2000.
The U.S., Global Change Research Information Office, "General effects on organisms," available at http://www.gcrio.org/UNEP1998/UNEP98p24.html, printed May 2, 2000.
Central Sydney Laboratory Service, "Gene Regulation Unit: Research," available at http://www.cs.nsw.gov.au/csls/KMI/methylation.html, printed Jun. 26, 2000.
Naylor, M.F. & Farmer, K.C., "The electronic textbook of dermatology, sun damage and protection," available at http://www.telemedicine.org/Sundam/sundam2.4.1.html, printed Jun. 26, 2000.
Naylor, M.F. & Farmer, K.C., "The electronic textbook of dermatology, sunscreens," available at http://www.telemedicine.org/Sundam/sundam2.4.2.html, printed Jun. 26, 2000.
Naylor, M.F. & Farmer, K.C., "The electronic textbook of dermatology, guidelines for minimizing uv exposure," available at http://www.telemedicine.org/Sundam/sundam2.4.3.html.

(Continued)

*Primary Examiner*—David Orzo
*Assistant Examiner*—Daniel M. Sullivan
(74) *Attorney, Agent, or Firm*—Baker Botts L.L.P.

(57) ABSTRACT

Sunscreen formulations containing nucleic acids are disclosed. The formulations can be used to reduce sunburns, the occurrence of skin cancer, and the occurrence of other ultraviolet radiation caused conditions. The nucleic acids are preferably DNA.

16 Claims, No Drawings

OTHER PUBLICATIONS

Juchem et al., "Health risks of ultraviolet radiation," Revista Da Sociedade Brasileira De Circurgia Plasticas, vol. 13, No. 2, 1998.

Safesun, "Personal uv meter, scientific data," available at http://www.safesun.com/scientific.html, printed May 9, 2000.

Ivillage, "Seasonal Considerations," available at http://www.ivillage.com/pets/features/purinadogcaretips/articles/0,4437,18301,00.html, printed May 12, 2000.

Ivillage, "Seasonal Considerations (continued)," available at http://www.ivillage.com/pets/features/purinadogcaretips/articles/0,4437,18301-2,00.html, printed May 12, 2000.

"Even pets can feel the burn,", available at http://www.ezio.freeserve.co.uk/burn.htm, printed May 11, 2000.

Salt Lake Tribune, "Exposure to any uv light carries a risk," Mar. 4, 1999.

Government of British Columbia, Ministry of Health and Ministry Responsible for Seniors, "Danger! Ultraviolet radiation exposure," available at http://www.hlth.gov.bc.ca/rpteb/ultra001.html, printed May 1, 2000.

Interlectric Corporation, "Tanning Process," available at http://www.interlectric.com/process.html.

"What is ultraviolet light?" available at http://www.am.qub.ac.uk/users/j.pelan/node2.html, printed May 1, 2000.

Alpha Nutriation, "Skin center: Sun, ultraviolet, photoaging," available at http://www.alphanutrition.com/skin/uvradiation.htm, printed May 1, 2000.

Gange et al., "efficacy of a sunscreen containing butyl methoxydibenzoylmethane against ultraviolet A radiation in photosensitized subjects," Journal of the Americasn Academy of Dermatology, vol. 15, No. 3, Sep. 1986, pp. 494–499.

About Face International, DNA, available at http://www.b-mdtrading.com/dnaa.htm?, printed Mar. 24, 2000.

* cited by examiner

SUNSCREEN FORMULATIONS CONTAINING NUCLEIC ACIDS

This application claims the benefit of U.S. Provisional Application No. 60/220,094, filed Jul. 21, 2000.

BACKGROUND OF THE INVENTION

Skin cancer (basal cell carcinoma, squamous cell carcinoma, and cutaneous melanoma) is the most common form of cancer in the United States. Approximately 90 percent of non-melanoma skin cancers are attributed to UV radiation. Absorption of solar radiation by the skin leads to DNA damage by the formation of cyclobutadiene pyrimidine dimers, pyrimidine (6,4) pyrimidone photoproducts, and single strand breaks.

UV radiation is conveniently divided into three groups ("bands"): UVA (320–400 nm), UVB (280–320 nm), and UVC (200–280 nm).

UVA radiation penetrates more deeply into the skin than does UVB, and leads to suntanning by oxidizing melanin in the skin to produce a dark pigment. UVA constitutes about 90% of UV radiation reaching the Earth's surface.

UVB constitutes about 10% of UV radiation reaching the Earth's surface. UVB radiation is the primary cause of sunburn and skin cancer. UVB is about 1000 times more potent in causing sunburn than is UVA.

UVC is not part of the tanning process. UVC is high energy UV radiation, and would cause significant damage to cells with which it contacted. Fortunately, UVC is absorbed by the Earth's atmosphere.

Sunscreen products are commonly given a sun protection factor "SPF" which correlates to the ability of the product to block UVB radiation. SPF is measured as the ratio of the amount of ultraviolet radiation required to produce minimal pinkness (erythema) in skin covered by a sunscreen, assessed 24 hours after exposure, to the amount of UV radiation required to produce a similar level of pinkness in unprotected skin. The SPF does not indicate the degree of UVA protection for a product.

Skin phototypes are rated on a scale of 1 to 6. The amount of UV radiation that may be absorbed by the skin without causing sunburn may be determined using the following table.

TABLE 1

Skin phototypes

| Skin phototype | Unexposed skin color | Minimum erythemal dose (MED) mJ/cm$^2$ |
| --- | --- | --- |
| 1 | White | 15–30 |
| 2 | White | 25–40 |
| 3 | White | 30–50 |
| 4 | Light brown | 40–60 |
| 5 | Brown | 60–90 |
| 6 | Dark brown or black | 90–150 |

Formulations useful for protection against UVA and/or UVB radiation can be divided into sunscreens and sunblocks. Sunscreens are spread onto the skin as an essentially invisible thin film. Sunblocks contain particulates such as titanium dioxide and zinc oxide which physically block ultraviolet radiation. Sunblocks provide broad protection against both UVB and UVA light. They can be cosmetically unacceptable to many people, because they are often messy, visible and do not easily wash off. Chemicals in sunscreens and sunblocks have come under scrutiny, as they have been suspected of generating free radicals.

Historically, various chemical agents have been used in oil, cream, and lotion sunscreen products. PABA (para-aminobenzoic acid) was one of the original ultraviolet B (UVB) protecting ingredients in sunscreens. Recently, PABA has been largely replaced by PABA esters (such as glycerol PABA, padimate A and padimate O) in sunscreens. PABA and PABA esters protect against UVB radiation, but not UVA radiation, the sun's burning rays that are the primary cause of sunburn and skin cancer. Additional commercial UVB blockers include salicylates, homomenthyl salicylate, cinnamates, octylmethoxycinnamate, cinoxate, benzophenones, oxybenzene, sulisobenzene, and anthranilates. UV scattering agents include zinc oxide, titanium dioxide, magnesium silicate, magnesium oxide, kaolin, ferrous oxide, ferric oxide, barium sulfate, and red petrolatum.

Chemicals which block UVA radiation include oxybensone, sulisobenzone and Parsol 1789 (avobenzone).

Various cosmetic formulations containing DNA have been proposed.

"DNA" is a skin restoration product by Wilma Schumann (distributed by About Face International, Inc.). The product contains deoxyribonucleic acid extracted from salmon roe. "DNA" is advertised as a treatment for combating stretch marks and acne. "DNA PLUS" is a gel emulsion of deoxyribonucleic acid, vitamin A, and vitamin E. The vitamins are suggested to protect the skin from the influences of the damaged ozone layer and from ultraviolet rays.

U.S. Pat. No. 5,547,684 describes cosmetic preparations containing DNA-sodium salt useful for the treatment of aging skin and skin problems. The DNA is extracted from various fish reproductive cells using a sodium chloride solution.

U.S. Pat. No. 5,985,333 describes the use of compositions containing DNA-sodium salt for burn and wound treatment. The compositions were proposed to be particularly useful for the treatment of burns resulting from radiation, such as those due to radiation therapy.

U.S. Pat. No. 5,662,889 describes oral compositions containing DNA-sodium salt. The compositions are proposed as mouthwash and toothpaste formulations.

U.S. Pat. No. 5,194,253 describes an aqueous gel containing alkaline salt or ammonium salt of hyaluronic acid, mineral or organic salt of high molecular weight DNA, and a hydrophilic polymer. The gel is proposed as a facial mask. The mask is alleged to have the following beneficial properties: powerful anti-wrinkle effect; improvement in the sebaceous secretion and regulation of the superficial hydrolipid film; considerable increase in the elasticity and in the firmness of the teguments; the effect of an exceptional increase in the freshness of the complexion; very effective photo-protection power; and favorable structural modifications, detectable by appropriate examination, of the dermo-epidermal constituents.

U.S. Pat. No. 4,707,354 describes sunscreen, protectant, and moisturizing dermatological compositions There exists a need for improved sunscreen formulations that confer protection from harmful ultraviolet radiation using biocompatible chemicals.

SUMMARY OF THE INVENTION

Sunscreen formulations containing nucleic acids are safe and effective in blocking hazardous ultraviolet rays. DNA is a preferred nucleic acid due to its relative stability. Commercial sources of DNA such as calf thymus and fish (e.g. salmon or herring) sperm are attractive due to their availability and low price. Methods of using such formulations to reduce or eliminate sunburning, skin cancer, and other deleterious effects of ultraviolet rays are also disclosed.

Definitions

The following definitions are provided in order to aid those skilled in the art in understanding the detailed description of the present invention.

"Nucleic acid" refers to DNA, RNA, synthetic DNA analogs, or synthetic RNA analogs.

"Sunburning" refers to the reddening of skin upon exposure to ultraviolet light (e.g. in sunlight). Sunburning can be quantitatively assayed by determining the time to burn (minutes or hours). Skin treated with a sunscreen formulation will have a longer time to burn as compared to the same skin lacking treatment with the sunscreen formulation. A superior sunscreen formulation will result in a longer time to burn than an inferior sunscreen formulation.

DETAILED DESCRIPTION OF THE INVENTION

Sunscreen Formulation Compositions

Each of the four nucleotide bases (A, C, G, and T) has a slightly different absorption spectrum, and the spectrum of DNA is the average of them. A solution of pure DNA appears transparent to the eye, and absorption doesn't become measurable until around 320 nm. The absorption peak of DNA is about 260 nm, followed by a dip between about 220 nm and 230 nm. The solution becomes essentially opaque in the far UV (FIG. 1). A 0.04 mg/mL solution of double stranded DNA has an absorbance ($OD_{260}$) of about 1.0 at 260 nm. Genomic DNA is reported to have 20 $OD_{260}$ units per milligram (Sigma Chemical Company, St. Louis, Mo.). Accordingly, compositions containing nucleic acids, and preferably containing DNA absorb the potentially dangerous UVB radiation (280–320 nm), while allowing UVA radiation (320–400 nm) to be absorbed by the skin. This absorbance profile reduces or eliminates sunburning and skin cancer, while allowing suntanning.

The invention can further take advantage of a property of DNA called hyperchromicity. As a double stranded DNA helix is degraded or denatured, the absorbance is increased by about 30 percent. Accordingly, as a sunscreen containing DNA is heated or degraded on the skin, the potential absorption of UVB radiation actually increases (FIG. 2).

DNA may be methylated to shift its absorbance spectrum. Methylation can be accomplished by enzymes (e.g. DNA methyltransferase) or by chemical reactions (e.g. methyl bromide). Methylated sites have been found to absorb higher levels of UVB radiation than unmethylated sites (Drouin, R. and Therrien, J.-P., *Photochem. & Photobiol. Rapd Comm.* 66: 719, 1997). Methylation of nucleic acids can be used to shift the absorbance spectrum such that more UVB radiation is absorbed than that absorbed by unmethylated nucleic acids.

Sunscreen formulations containing nucleic acids, and preferably containing DNA act as "sacrificial DNA" by presenting a layer of DNA which absorbs dangerous UVB radiation that would be otherwise absorbed by the skin. DNA or RNA can be large polymers or shorter oligomers. Moderate to short length nucleic acids can be produced by degradation of large polymeric nucleic acids (e.g. by sonication or mechanical shearing), by enzymatic processes (e.g. by restriction endonucleases), or by chemical synthesis.

The size of nucleic acids are commonly referred to by the number of bases (for single stranded nucleic acids, such as RNA) or number of base pairs (for double stranded nucleic acids, such as DNA). The size of the nucleic acids for use in sunscreen formulations can generally be any size, and preferably have an average (number average or weight average) greater than about: 100 base pairs, about 250 base pairs, about 500 base pairs, 750 base pairs, 1000 base pairs, 2500 base pairs, 5000 base pairs, or 10000 base pairs. The size of nucleic acids can conveniently be measured using agarose gel electrophoresis or polyacrylamide gel electrophoresis. Nucleic acid oligomers can generally be any size, including 8 mers, 10 mers, 12 mers, 14 mers, 16 mers, 18 mers, 20 mers, 22 mers, 24 mers, 26 mers, 28 mers, 30 mers, and so on. The nucleic acids can be one or more of different forms of nucleic acids, e.g. cholesteric liquid crystal phase, lyotropic liquid crystal phase, precholesteric phase, single strand, double strand, or triple strand.

The concentration of nucleic acids in the sunscreen formulations can generally be any concentration, and preferably is greater than about 0.01% (w/v), greater than about 0.05% (w/v), greater than about 0.1% (w/v), greater than about 0.25% (w/v), greater than about 0.5% (w/v), greater than about 0.75% (w/v), greater than about 1% (w/v), greater than about 2% (w/v), greater than about 3% (w/v), greater than about 4% (w/v), greater than about 5% (w/v), greater than about 6% (w/v), greater than about 7% (w/v), greater than about 8% (w/v), greater than about 9% (w/v), or greater than about 10% (w/v). Alternatively, the concentrations can be expressed as milligrams per liter. The concentration of nucleic acids in the sunscreen formulations can be such that the nucleic acids are soluble in the sunscreen formulations, or that the nucleic acids are insoluble in the sunscreen formulations.

The intensity of UV radiation can be measured in joules/$m^2$. The inventive sunscreen formulation preferably reduces the intensity of UV radiation absorbed by the skin of a treated mammal by at least about 50%, at least about 60%, at least about 70%, at least about 80%, at least about 90%, at least about 95%, at least about 97.5%, at least about 99%, and ideally about 100% as compared to the intensity of UV radiation absorbed by the skin of an untreated mammal of the same species. The UV radiation absorbed by the sunscreen formulation is preferably UVB radiation, and the absorption of UVB radiation can conveniently be assayed at 280 nm. The absorbance or transmittance can be measured using a thin film of sunscreen formulation in a UV spectrometer, as compared to a blank control sample lacking nucleic acids.

The sunscreen formulations can further comprise additional materials such as perfumes or dyes. The formulations can further comprise aloe or sorbitol. The sunscreen formulations can be a liquid, a gel, a cream, an aerosol spray, or any other commercially acceptable formulation. The formulations can contain water, ethyl alcohol, isopropyl alcohol, or other alcohols that evaporate once the formulation has been applied to the skin.

The sunscreen formulations can further comprise water, alcohols, water-soluble alcohols such as ethanol or 2-propanol, DMSO, antifungal agents, antibacterial agents, or buffers such as PBS or HEPES. Additional UV absorbing materials can be added such as apurinic acid, xanthines, purines, uric acid, glycosylated forms, substituted forms, and polymeric forms thereof. Aromatic amino acids such as phenylalanine, tryptophan, and tyrosine can be added to the sunscreen formulations. Proteins which are rich in aromatic amino acids can be added to the sunscreen formulations.

Examples of such proteins include keratin and albumin. Collagen, elastin, riboflavin (vitamin D), or retinoic acid can be added to the sunscreen formulations.

The sunscreen formulations can additionally be used as aftershave lotions, colognes, perfumes, skin moisturizers, and so on.

Methods of Use

The above described sunscreen formulations can be used on the skin of generally any mammal. Preferably, the sunscreen formulations are to be used on the skin of humans. The sunscreen formulations can alternatively be used on cats, dogs, rabbits, horses, cows, sheep, pigs, mink, or other mammals which are exposed to sunlight. Comparisons between treatment with a sunscreen formulation as described in the invention and a lack of such treatment are performed with identical intensity of ultraviolet radiation for an identical amount of time of exposure.

The above described sunscreen formulations can be used in a method to reduce the absorption of ultraviolet radiation by the skin of a mammal treated with the formulations, as compared to the absorption of ultraviolet radiation by the skin of the same species of mammal not treated with the formulations. The method preferably comprises providing a sunscreen formulation comprising nucleic acids; and applying the sunscreen formulation to the skin of an untreated mammal to obtain a treated mammal; wherein: the amount of ultraviolet radiation absorbed by the skin of the treated mammal is less than the amount of ultraviolet radiation absorbed by the skin of the untreated mammal. The amount of ultraviolet radiation absorbed by the skin is preferably assayed by the absorbance or transmittance of ultraviolet radiation having a wavelength of 280 nm. The amount of absorbance of ultraviolet radiation by the sunscreen formulation is preferably at least about 50%, at least about 60%, at least about 70%, at least about 80%, at least about 90%, at least about 95%, at least about 97.5%, at least about 99%, and ideally about 100%. The amount of ultraviolet radiation absorbed by the skin can be calculated by subtracting the absorbance of the sunscreen formulation from 100%. For example, if the sunscreen formulation absorbs 85% of the ultraviolet radiation, then the skin absorbs 15%. The skin of the treated mammal preferably absorbs less ultraviolet radiation than does the skin of the untreated mammal. The skin of the treated mammal preferably absorbs less than 10%, less than 5%, less than 1%, less than 0.5%, or less than 0.1% of the ultraviolet radiation absorbed by the skin of the untreated mammal. The nucleic acids are preferably DNA. The ultraviolet radiation absorbed by the nucleic acids is preferably UVB radiation.

The above described sunscreen formulations can be used in a method to reduce the occurrence of skin cancer on a mammal treated with the formulations, as compared to the occurrence of skin cancer on the same species of mammal not treated with the formulations. The method comprises providing a sunscreen formulation comprising nucleic acids; and applying the sunscreen formulation to the skin of an untreated mammal to obtain a treated mammal; wherein the occurrence of skin cancer on the treated mammal is less than the occurrence of skin cancer on the untreated mammal. The occurrence of skin cancer on the treated mammal is preferably less than about 50%, less than about 40%, less than about 30%, less than about 25%, less than about 20%, less than about 10%, less than about 5%, or less than about 1% of the occurrence of skin cancer on the untreated mammal.

The above described sunscreen formulations can be used in a method to reduce the sunburning of a mammal treated with the formulations, as compared to the sunburning of the same species of mammal not treated with the formulations. The method comprises providing a sunscreen formulation comprising nucleic acids; and applying the sunscreen formulation to the skin of an untreated mammal to obtain a treated mammal; wherein the sunburning of the treated mammal is less than the sunburning of the untreated mammal. The sunburning of the treated mammal is preferably less than about 50%, less than about 40%, less than about 30%, less than about 25%, less than about 20%, less than about 10%, less than about 5%, or less than about 1% of the sunburning of the untreated mammal. The reduction in sunburning preferably reduces the UV radiation absorbed by the skin of the mammal to below the minimum erythemal dose for a period of exposure time of 1 hour, 2 hours, 3 hours, 4 hours, 5 hours, 6 hours, 7 hours, and most preferably 8 hours. The minimum erythemal dose varies according to the skin phototype of the mammal, as described above in Table 1.

The above described sunscreen formulations can be used in additional applications for treatment of conditions caused by ultraviolet radiation. Sunscreen formulations can be used to minimize or eliminate facial-oral herpes simplex recurrent herpes labialis or cold sores. Sunscreen formulations can be used to reduce or eliminate the occurrence of Lentigo solar, commonly referred to as "liver spots" or "coffin spots". Sunscreen formulations can be used to reduce or eliminate the occurrence of Cutis Rhomboidalis Nuchae. Sunscreen formulations can be used to reduce or eliminate the occurrence of Favre-Racouchot disease. Sunscreen formulations can be used to reduce or eliminate the occurrence of Solar Purpura (Batema's Senile Purpura). Sunscreen formulations can be used to reduce or eliminate the occurrence of Venous Lake. Sunscreen formulations can be used to reduce or eliminate the occurrence of stellate scars of the hands and forearms resulting from tearing of fragile photodamaged skin. Sunscreen formulations can be used to reduce or eliminate the occurrence of Chromic actinic dermatitis. Sunscreen formulations can be used to reduce or eliminate the occurrence of xeroderma pigmentosum. Sunscreen formulations can be used to reduce or eliminate the occurrence of solar urticaria. Sunscreen formulations can be used to reduce or eliminate the occurrence of chronic discoid lupus erythematosis. Sunscreen formulations can be used to reduce or eliminate the occurrence of photoaging. Sunscreen formulations can be used to reduce or eliminate the occurrence of pellagra.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Sunscreen Formulations

Sunscreen formulations have been prepared containing 0.01%, 0.1%, 1%, 3%, 5%, and 10% herring sperm DNA (ICN Biomedicals Inc., Costa Mesa, Calif.). The formulations contained 0%, 1%, 10%, 20%, or 50% ethanol. All formulations were stable at room temperature, and were effective at preventing sunburn during ordinary outdoor exposure of human skin in San Antonio, Tex.

Example 2

Percent Transmission of 260 nm Ultraviolet Radiation

Solutions of DNA were made in 150 mM PBS buffer, pH 7.1. The percent transmission at 260 nm was measured using a Beckman spectrometer, relative to a blank control of PBS buffer.

TABLE 2

Transmission of DNA solutions at 260 nm

| DNA concentration | Percent transmission |
| --- | --- |
| 0.1 mM | 27 |
| 1 mM | 0.02 |
| 5 mM | 0 |
| 10 mM | 0 |

Example 3

Absorption of Ultraviolet Radiation by DNA in PBS and HEPES Buffers

Measurements of the UV-spectral absorbance of DNA were taken for three concentrations of DNA in two different buffers. The buffers used were a 5.0 mM HEPES and 100 mM PBS (corresponding to 13.7 mM NaCl).

The 5.0 mM HEPES buffer was made from a 1 M stock solution of HEPES (Cellgro, Herndon, Va.). 250 µL of the stock solution were placed in 40 mL of distilled water. The pH of the diluted solution was adjusted to 7.0 with 0.1 M NaOH. The pH-adjusted diluted solution was transferred to a 50 mL volumetric flask and the final volume was made 50 mL with distilled water.

The 100 mM PBS solution was made from a stock solution of 1 M PBS (137 mM NaCl, 2.7 mM KCl, 4.3 mM $Na_2HPO_4 \cdot 7H_2O$, 1.4 mM $KH_2PO_4$). 5 mL of the stock solution were added to 40 mL of distilled water. The pH of the diluted solution was adjusted to 7.3 with 0.1 M NaOH. The pH-adjusted diluted solution was transferred to a 50 mL volumetric flask and the final volume was made 50 mL with distilled water.

DNA solutions were made using fish sperm DNA-sodium salt (ICN Biomedicals Inc., Costa Mesa, Calif.). The assumed molar mass of the DNA was 340 g/mole. A 30 mM solution of DNA was created by dissolving 30.6 mg of DNA in 3 mL of buffer solution. The DNA was allowed to dissolve in the buffer under gentle rocking for 2 hours at room temperature. Two dilution series were made using the 100 mM PBS and 5 mM HEPES buffers. The dilution series consisted of 20, 10, 5, 0.1, and 0.05 mM DNA solutions.

Measurement of the UV-spectral absorbance was conducted using a HP UV/Vis spectral photometer. The scan range was set to 200–350 nm at 2 nm increments. The base line (blank) was established using the corresponding buffer for each of the dilution series. The 20 and 10 mM DNA solutions for each of the buffers gave absorbance reading that were beyond the range of the spectrometer. Only data collected from the 5, 0.1, and 0.05 mM DNA solutions were recorded. The absorbance data in the following two tables has been rounded to the nearest 0.01 number. The data is graphically represented in FIGS. 3 and 4.

TABLE 3

| | PBS buffer | | |
| --- | --- | --- | --- |
| Wavelength (nm) | 0.05 mM DNA | 0.1 mM DNA | 5 mM DNA |
| 200 | 0.00 | −0.01 | −0.04 |
| 202 | 0.27 | 0.16 | 0.36 |
| 204 | 0.11 | 0.03 | −0.14 |
| 206 | −0.12 | 0.18 | −0.08 |
| 208 | −0.06 | 0.04 | 0.08 |
| 210 | −0.07 | −0.10 | 0.28 |
| 212 | −0.06 | −0.01 | 0.01 |
| 214 | 0.33 | 0.38 | 0.56 |
| 216 | 0.12 | 0.33 | 0.49 |
| 218 | −0.31 | −0.29 | −0.15 |
| 220 | 0.00 | −0.12 | 0.19 |
| 222 | −0.01 | 0.03 | 0.37 |
| 224 | 0.10 | −0.02 | 0.13 |
| 226 | 0.18 | 0.36 | 0.66 |
| 228 | 0.07 | 0.21 | 0.07 |
| 230 | −0.04 | 0.03 | −0.01 |
| 232 | −0.06 | 0.02 | 0.08 |
| 234 | 0.34 | 0.17 | 0.48 |
| 236 | −0.10 | 0.01 | 0.30 |
| 238 | 0.32 | 0.34 | 0.64 |
| 240 | 0.20 | 0.23 | 0.55 |
| 242 | 0.03 | 0.10 | 0.49 |
| 244 | 0.13 | 0.26 | 0.94 |
| 246 | 0.19 | 0.42 | 1.32 |
| 248 | 0.18 | 0.41 | 1.47 |
| 250 | 0.23 | 0.51 | 2.07 |
| 252 | 0.23 | 0.54 | 1.78 |
| 254 | 0.24 | 0.56 | 2.00 |
| 256 | 0.25 | 0.58 | 2.29 |
| 258 | 0.26 | 0.59 | 2.66 |
| 260 | 0.26 | 0.60 | 3.03 |
| 262 | 0.26 | 0.59 | 2.78 |
| 264 | 0.25 | 0.58 | 2.72 |
| 266 | 0.24 | 0.56 | 2.82 |
| 268 | 0.23 | 0.54 | 2.93 |
| 270 | 0.22 | 0.51 | 3.24 |
| 272 | 0.21 | 0.48 | 3.09 |
| 274 | 0.19 | 0.45 | 2.91 |
| 276 | 0.18 | 0.41 | 2.68 |
| 278 | 0.16 | 0.37 | 2.57 |
| 280 | 0.14 | 0.34 | 2.54 |
| 282 | 0.13 | 0.30 | 2.48 |
| 284 | 0.11 | 0.26 | 2.41 |
| 286 | 0.09 | 0.22 | 2.39 |
| 288 | 0.07 | 0.18 | 2.31 |
| 290 | 0.06 | 0.14 | 2.30 |
| 292 | 0.04 | 0.11 | 2.31 |
| 294 | 0.03 | 0.08 | 2.23 |
| 296 | 0.02 | 0.06 | 1.97 |
| 298 | 0.01 | 0.03 | 1.52 |
| 300 | 0.00 | 0.02 | 1.11 |
| 302 | 0.00 | 0.01 | 0.82 |
| 304 | 0.00 | 0.00 | 0.61 |
| 306 | 0.00 | 0.00 | 0.48 |
| 308 | 0.00 | 0.00 | 0.39 |
| 310 | 0.00 | 0.00 | 0.34 |
| 312 | 0.00 | 0.00 | 0.31 |
| 314 | 0.00 | 0.00 | 0.29 |
| 316 | 0.00 | 0.00 | 0.28 |
| 318 | 0.00 | 0.00 | 0.26 |
| 320 | 0.00 | 0.00 | 0.26 |
| 322 | 0.00 | 0.00 | 0.25 |
| 324 | 0.00 | 0.00 | 0.24 |
| 326 | 0.00 | 0.00 | 0.24 |
| 328 | 0.00 | 0.00 | 0.23 |
| 330 | 0.00 | 0.00 | 0.23 |
| 332 | 0.00 | 0.00 | 0.22 |
| 334 | 0.00 | 0.00 | 0.22 |
| 336 | 0.00 | 0.00 | 0.21 |
| 338 | 0.00 | 0.00 | 0.21 |
| 340 | 0.00 | 0.00 | 0.21 |
| 342 | 0.00 | 0.00 | 0.20 |

TABLE 3-continued

PBS buffer

| Wavelength (nm) | 0.05 mM DNA | 0.1 mM DNA | 5 mM DNA |
|---|---|---|---|
| 344 | 0.00 | 0.00 | 0.20 |
| 346 | 0.00 | 0.00 | 0.20 |
| 348 | 0.00 | 0.00 | 0.19 |
| 350 | 0.00 | 0.00 | 0.19 |

TABLE 4

HEPES buffer

| Wavelength (nm) | 0.05 mM DNA | 0.1 mM DNA | 5 mM DNA |
|---|---|---|---|
| 200 | 0.09 | 0 | 0.16 |
| 202 | 0.00 | 0.24 | 0.23 |
| 204 | −0.44 | −0.18 | −0.28 |
| 206 | 0.20 | 0.32 | 0.52 |
| 208 | 0.50 | 0.27 | 0.12 |
| 210 | −0.16 | −0.28 | −0.29 |
| 212 | 0.29 | −0.10 | −0.07 |
| 214 | 0.05 | 0.19 | 0.30 |
| 216 | −0.17 | −0.07 | 0.04 |
| 218 | −0.04 | 0.36 | 0.15 |
| 220 | 0.55 | 0.44 | 0.38 |
| 222 | −0.25 | −0.39 | −0.35 |
| 224 | −0.02 | 0.00 | 0.16 |
| 226 | 0.10 | 0.26 | 0.25 |
| 228 | −0.39 | −0.22 | −0.22 |
| 230 | 0.21 | 0.42 | 0.67 |
| 232 | 0.21 | 0.03 | 0.17 |
| 234 | 0.08 | −0.15 | −0.08 |
| 236 | 0.12 | 0.06 | 0.26 |
| 238 | 0.19 | 0.37 | 0.47 |
| 240 | 0.06 | 0.17 | 0.68 |
| 242 | 0.19 | 0.48 | 0.78 |
| 244 | 0.26 | 0.40 | 0.86 |
| 246 | 0.21 | 0.36 | 0.99 |
| 248 | 0.24 | 0.51 | 1.41 |
| 250 | 0.26 | 0.54 | 1.62 |
| 252 | 0.29 | 0.59 | 2.14 |
| 254 | 0.31 | 0.61 | 2.12 |
| 256 | 0.32 | 0.63 | 2.17 |
| 258 | 0.32 | 0.64 | 2.44 |
| 260 | 0.32 | 0.65 | 2.60 |
| 262 | 0.32 | 0.64 | 2.77 |
| 264 | 0.31 | 0.63 | 3.25 |
| 266 | 0.31 | 0.61 | 3.01 |
| 268 | 0.29 | 0.59 | 2.86 |
| 270 | 0.28 | 0.56 | 2.74 |
| 272 | 0.26 | 0.53 | 2.86 |
| 274 | 0.25 | 0.49 | 2.87 |
| 276 | 0.23 | 0.45 | 2.76 |
| 278 | 0.20 | 0.41 | 2.56 |
| 280 | 0.18 | 0.37 | 2.38 |
| 282 | 0.16 | 0.32 | 2.31 |
| 284 | 0.14 | 0.28 | 2.31 |
| 286 | 0.12 | 0.24 | 2.26 |
| 288 | 0.10 | 0.20 | 2.25 |
| 290 | 0.08 | 0.15 | 2.26 |
| 292 | 0.06 | 0.12 | 2.18 |
| 294 | 0.04 | 0.09 | 2.15 |
| 296 | 0.03 | 0.06 | 1.93 |
| 298 | 0.02 | 0.04 | 1.50 |
| 300 | 0.01 | 0.03 | 1.07 |
| 302 | 0.00 | 0.02 | 0.74 |
| 304 | 0.00 | 0.01 | 0.52 |
| 306 | 0.00 | 0.00 | 0.38 |
| 308 | 0.00 | 0.00 | 0.29 |
| 310 | 0.00 | 0.00 | 0.24 |
| 312 | 0.00 | 0.00 | 0.21 |
| 314 | 0.00 | 0.00 | 0.19 |
| 316 | 0.00 | 0.00 | 0.17 |
| 318 | 0.00 | 0.00 | 0.16 |
| 320 | 0.00 | 0.00 | 0.16 |
| 322 | 0.00 | 0.00 | 0.15 |
| 324 | 0.00 | 0.00 | 0.15 |
| 326 | 0.00 | 0.00 | 0.14 |
| 328 | 0.00 | 0.00 | 0.14 |
| 330 | 0.00 | 0.00 | 0.14 |
| 332 | 0.00 | 0.00 | 0.13 |
| 334 | 0.00 | 0.00 | 0.13 |
| 336 | 0.00 | 0.00 | 0.13 |
| 338 | 0.00 | 0.00 | 0.13 |
| 340 | 0.00 | 0.00 | 0.12 |
| 342 | 0.00 | 0.00 | 0.12 |
| 344 | 0.00 | 0.00 | 0.12 |
| 346 | 0.00 | 0.00 | 0.12 |
| 348 | 0.00 | 0.00 | 0.12 |
| 350 | 0.00 | 0.00 | 0.12 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A method to reduce the absorption of ultraviolet radiation by the skin of a mammal, the method comprising:
   applying a formulation consisting essentially of DNA of an average size of at least about 10,000 base pairs to the skin of a mammal to reduce the absorption of ultraviolet radiation by the skin of said mammal.

2. The method of claim 1, wherein the ultraviolet radiation is UVB radiation.

3. The method of claim 1, wherein applying said formulation to said mammal results in a reduction in the amount of ultraviolet radiation absorbed by the skin of said mammal.

4. The method of claim 1, wherein applying said formulation to said mammal results in at least about a 90% reduction in the amount of ultraviolet radiation absorbed by the skin of said mammal.

5. The method of claim 1, wherein applying said formulation results in at least about a 95% reduction in the amount of ultraviolet radiation absorbed by the skin of said mammal.

6. The method of claim 1, wherein applying said formulation results in at least about a 99% reduction in the amount of ultraviolet radiation absorbed by the skin of said mammal.

7. The method of claim 1, wherein the ultraviolet radiation absorbed by the skin of the mammal is less than a minimum erythemal dose for the mammal after a one hour exposure to the ultraviolet radiation.

8. The method of claim 1, wherein the ultraviolet radiation absorbed by the skin of the mammal is less than a minimum erythemal dose for the mammal after a four hour exposure to the ultraviolet radiation.

9. The method of claim 1, wherein the ultraviolet radiation absorbed by the skin of the mammal is less than a minimum erythemal dose for the mammal after an eight hour exposure to the ultraviolet radiation.

10. The method of claim 1, wherein the mammal is human.

11. The method of claim 1, wherein the mammal is a dog or a cat.

12. The method of claim 1, wherein the formulation further comprises a compound selected from the group consisting of phenylalanine, tryptophan, tyrosine, keratin, albumin, collagen, elastin, riboflavin, and retinoic acid.

13. The method of claim 1, wherein the DNA is methylated.

14. The method of claim 1, wherein the nucleic acids are in a cholesteric liquid phase, a lyotropic liquid crystal phase, or a precholesteric phase.

15. The method of claim 1, wherein the formulation further comprises a compound selected from the group consisting of apurinic acids, purines, and uric acids.

16. The method of claim 1, wherein the formulation further comprises a compound selected from the group consisting of water, alcohols, water-soluble alcohols, dimethyl sulfoxide, antifungal agents, antibacterial agents, buffers, perfumes, dyes, aloe, and sorbitols.

* * * * *